(12) United States Patent
Lipsky et al.

(10) Patent No.: US 10,242,158 B2
(45) Date of Patent: Mar. 26, 2019

(54) UNIVERSAL CHARGE ROUTING SYSTEM FOR MEDICAL BILLING

(71) Applicant: Epic Systems Corporation, Verona, WI (US)

(72) Inventors: Mark Robert Lipsky, Waunakee, WI (US); Alexandre Sena Keresztes, Middleton, WI (US); Dazhi Li, Madison, WI (US); Biao Shou, Madison, WI (US); Herman Harjono, Cupertino, CA (US); Jagdeesh Shukla, Oswego, IL (US); Brandon Jon Baldock, Fitchburg, WI (US); Ting-Sheng Fu, Madison, WI (US); Tin-Hang Andrew Ma, Fitchburg, WI (US); Nishant Upadhyaya

(73) Assignee: Epic Systems Corporation, Verona, WI (US)

( * ) Notice: Subject to any disclaimer, the term of this patent is extended or adjusted under 35 U.S.C. 154(b) by 50 days.

(21) Appl. No.: 14/109,370

(22) Filed: Dec. 17, 2013

(65) Prior Publication Data

US 2014/0108038 A1 Apr. 17, 2014

Related U.S. Application Data

(62) Division of application No. 10/950,882, filed on Sep. 27, 2004, now Pat. No. 8,615,403.

(51) Int. Cl.
*G06Q 10/00* (2012.01)
*G06F 19/00* (2018.01)
*G06Q 30/04* (2012.01)
*G06Q 50/22* (2018.01)

(52) U.S. Cl.
CPC ............ *G06F 19/328* (2013.01); *G06F 19/00* (2013.01); *G06Q 30/04* (2013.01); *G06Q 50/22* (2013.01)

(58) Field of Classification Search
CPC ...... G06Q 10/10; G06Q 10/06; G06Q 20/102; G06Q 50/22; G06Q 30/04; G06Q 50/24; G16H 10/60; G16H 15/00; G16H 80/00; G06F 19/321; G06F 19/3456; G06F 19/00
See application file for complete search history.

(56) References Cited

U.S. PATENT DOCUMENTS 7,020,618 B1 * 3/2006 Ward .................... 705/2
2002/0111829 A1 * 8/2002 Robibero ............... 705/3

* cited by examiner

*Primary Examiner* — Maroun P Kanaan
(74) *Attorney, Agent, or Firm* — Boyle Fredrickson, S.C.

(57) ABSTRACT

A medical charge router receives charge information from a variety of sources and converts it to a standard charge format for automated processing and routing to one of multiple billing programs.

25 Claims, 4 Drawing Sheets

UNIVERSAL CHARGE ROUTING SYSTEM FOR MEDICAL BILLING

CROSS-REFERENCE TO RELATED APPLICATION

This divisional application claims priority to U.S. Non-Provisional patent application Ser. No. 10/950,882 entitled "Universal Charge Routing System for Medical Billing," filed Sep. 27, 2004, the disclosure of which is hereby expressly incorporated herein by reference.

BACKGROUND OF THE INVENTION

The present invention relates to medical billing systems and in particular to a charge router centrally collecting medical charge information and distributing it to different billing programs.

Hospitals and physicians deliver healthcare cooperatively, but as separate business entities. A patient staying in a hospital will typically receive separate bills from a treating physician, from the hospital, and from other sources as providing care may dictate. A physician's charges may cover the physician's professional services, the hospital's may cover use of hospital resources including rooms, equipment, and supplies, and other sources may include independent services run within the hospital, such as a home health care organization run by an independent entity. When separate physicians render services during a hospital stay, for example, a surgeon, an anesthesiologist, and a radiologist, each physician may generate charges resulting in separate bills. Even when physicians and hospitals work as a single business entity in an integrated delivery network, separate billing systems may be required by the payors.

Bills from each business entity are normally generated using computerized billing programs. These billing programs accept charges from submitting programs running on one or more remote terminals and operated by hospital or physician staff. The billing programs collect the charges, and edits and reviews the charges, ultimately producing a printed bill or its equivalent to be mailed or sent to a payor. Different business entities often use different the billing programs provided by different vendors and each having their own proprietary submitting programs and charge data protocols.

If charges are submitted to the wrong billing program, the erroneous charge may have to be manually deleted and the person originally submitting the charge instructed to resubmit the charge to the correct billing program. Manual corrections significantly delay the billing process, but automatic correction or deletion of erroneously directed charge information is hampered by lack of compatibility among billing and submitting programs. When a medical procedure generates charges destined for two different billing programs, a correction of an error in one charge detected by one billing program or made by the charge source does not automatically lead to a correction of the other charge.

Some charges may require a synoptic view of other related charges processed by other billing programs. For example, the charging of vaccination shots may be based on a count of the sequence number of the shot. If the shots are provided by different facilities having different billing systems, this count may be difficult to determine. Under certain reimbursement rules, different charge rules may apply to medical treatment received in a clinic depending on whether the treatment is shortly thereafter continued in a hospital. These rules are difficult to implement automatically if different billing programs are used by the clinic and hospital.

One possible solution is for all health care providers to adopt a single billing program or a common standard for billing programs that would allow them to freely intercommunicate. Such interoperability is not likely in the near future.

BRIEF SUMMARY OF THE INVENTION

The present invention provides a charge router that stands among multiple systems creating charges and billing programs that receive and process those charges, possibly from different vendors, to collect all charges at a common point and then distribute the charges to particular billing programs. By passing all charges through a common point, processing and correction of charges can be done with a single set of rules, and by having access to a universal view of all charges, more sophisticated and automatic rules can be implemented. Access to all charges also allows the generation of a comprehensive charge log allowing changes and modifications to charges to be simply implemented without compatibility between a variety of billing systems and from a variety of sources. This centralization of charge processing may be accomplished by translating charges from a variety of different proprietary submitting programs into a universal charge format that may be processed and then converted back into the necessary billing software format for a designated billing program.

Specifically then, the present invention provides a charge router for use in medical billing systems. The charge router includes a set of input translators receiving charges to convert the charge data of the charges to universal charges having a common format. A destination rule engine analyzes the universal charges to determine a destination billing program. A set of output translators then receives the universal charges and their destinations from the destination rule engine and converts the universal charges to a proper billing program format according to the destination billing program.

It is thus one object of an embodiment of the invention to provide the benefits of a universal processing of charges for a medical procedure which generates bills through many possibly incompatible billing programs.

The destination rule engine may deduce the destinations for each charge from charge data describing the medical procedure.

Thus, it is another object of an embodiment of the invention to permit the routing of charges when the charges do not, on their face, identify a destination billing program.

The rule engine may insert the identified destination into the universal charge from which the destination is derived.

Thus, it is another object of an embodiment of the invention to create a complete signature of the charge that may be used for subsequent logging and correction.

The destination rule engine may include a rule editor receiving commands from a user to edit the rules of the destination rule editor.

It is thus another object of an embodiment of the invention to provide a program that is easily customized by the user.

The charge router may provide for a work-queue rule engine identifying universal charges that require human review and enrolling these universal charges in a work-queue for review by a human operator before forwarding the universal charges to an output translator.

It is thus another object of an embodiment of the invention to provide for a single point for identifying and correcting ambiguities and errors in charges which permits prioritization and monitoring of the corrections.

The charge router may further include an error pool receiving universal charges that cannot be processed by the destination rule engine, or other rule engines or components of the charge router, for review by a human operator without forwarding the charge data to an output translator.

It is thus another object of an embodiment of the invention to provide a separate pool for logical errors possible when rules are generated by individual users.

The charge router may further include a modification rule engine analyzing the charge data of the universal charges to modify the universal charges before forwarding the universal charges to an output translator. The modification may be the replacement of a portion of the charge data with different charge data or the addition or elimination of charge data or the creation of a new universal charge by splitting a single universal charge, or the holding of a charge for a period of time.

Thus, it is another object of an embodiment of the invention to provide for a wide variety of automatic modification of the charges.

The modification may be based on information from different universal charges destined for different billing systems.

Thus, it is another object of at least one embodiment of the invention to allow sophisticated processing of charge data requiring information normally residing in incompatible billing programs.

The modification rule engine may include an editor for a user to edit test sections and macro sections used in the modification rule editor.

Thus, it is another object of an embodiment of the invention to provide a standard program that nevertheless allows a user to edit the modification rules.

The charge router may include an administrative data processor collecting data on the flow of charges through the charge router to create a report providing data fields selected from the group consisting of a number of correctly processed charges, delayed charges, erroneous charges, history of the work-queue, distribution of charges among billing programs.

Thus, it is another object of an embodiment of the invention to provide improved administrative oversight of a billing process normally spread among different billing programs. In particular, the present invention allows the generation of a single report to show charges from multiple sources and billing systems instead of separate reports run by source and billing systems.

More generally, the present invention provides a medical billing system connecting charge sources to a common data receiving point and billing programs to a common data providing point. An electronic computer collects all charge data from the charge sources and selectively directs charge data to ones of the billing programs while logging at least a portion of the charge data. In response to a query identifying charge data, the computer provides records from the log matching the portion of the charge data together with the destination.

Thus, it is another object of an embodiment of the invention to provide a universal view of the charging process that may be stored and searched for correction of complex transactions involving multiple billing programs and submitters.

The query may be associated with a change of a charge and the electronic computer may forward a changed message to the destination billing programs identified in the query response.

Thus, it is an object of an embodiment of the invention to facilitate the transmission of change messages in complex multi-billing program processes.

These particular objects and advantages may apply to only some embodiments falling within the claims and thus do not define the scope of the invention.

DETAILED DESCRIPTION OF THE PREFERRED EMBODIMENT

Figure 1:
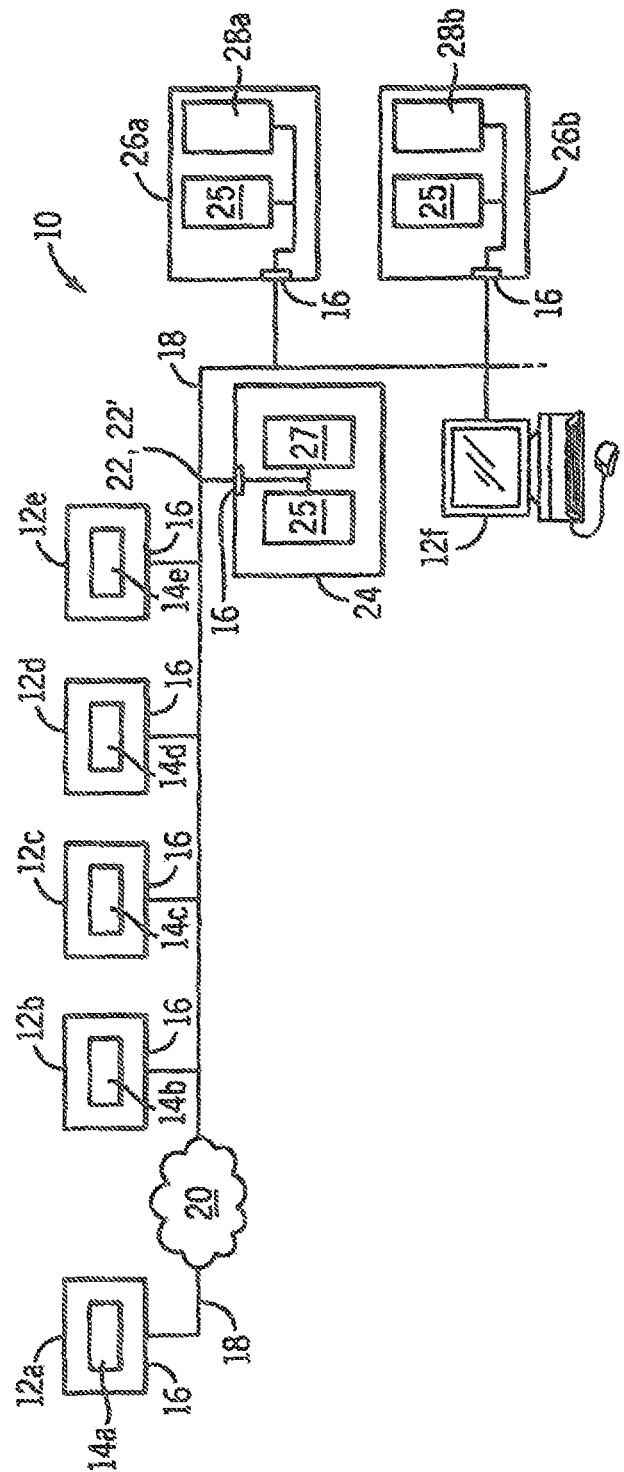
FIG. 1 is a physical block diagram of a billing system of the present invention as implemented in one embodiment as a set of computers connected by a common communication network.

Referring now to FIG. 1, a medical billing system 10 may include a number of billing terminals 12a through 12d, each being a computer terminal associated, for example, with a hospital service area, a medical laboratory, and/or a professional office of a physician.

Each of the terminals 12a through 12d may execute a submitting program 14a through 14d such as provides a graphical interface through which a user may enter charge data associated with a medical procedure. The submitting programs 14a forward the charge data to billing programs 28a and 28b such as may be held on remote billing computers 26a and 26b executed by processors 25. Generally, each of the submitting programs 14a through 14d is associated with a single specific billing program 28a or 28b such as commonly may be either a hospital billing system or professional billing program. Usually the billing programs 28 also incorporate components similar to programs 14 that may be used to directly enter billing data.

The terminals 12a through 12d each include network interfaces 16 allowing them to connect to a network 18, for example, an Ethernet network, also communicating with the billing computers 26a and 26b through interfaces 16. The network 18 is of arbitrary topology provided that it connects each of the terminals 12a through 12d to a common logical point 22 and each of billing computers 26a and 26b to a common logical point 22' (in this case the same physical point). Generally, the network 18 may include bridges, connections over the Internet 20, wireless links, dedicated fines, and other well known methods of data communication.

The common logical points 22 and 22' communicate with at least one network interface 16 of a computer 24 holding a charge router program 27 executed by a processor 25. As will be described in more detail below, the charge router program 27 receives charge data from the terminals 12a through 12d over the network 18, processes that charge data, and distributes charge data through network 18 to billing computers 26a and 26b. Other terminals 12f may also be connected to the network 18 or directly to the charge router computer 24 to provide communications with the charge router program 27 as will be described.

It will be understood to those of ordinary skill in the art that the physical structure shown may be readily varied. Additional billing computers 26 and/or billing programs 28 may be added and the physical network may be modified to provide the necessary communication using single or multiple links as will be understood to those of ordinary skill in the art. Terminals 12 and submitting programs 14 may be added or removed. Multiple programs, including the charge router program 27, may run on a single computer, and other similar changes in how the programs are distributed among hardware may be made without fundamentally affecting the operation of the invention.

Figure 2:
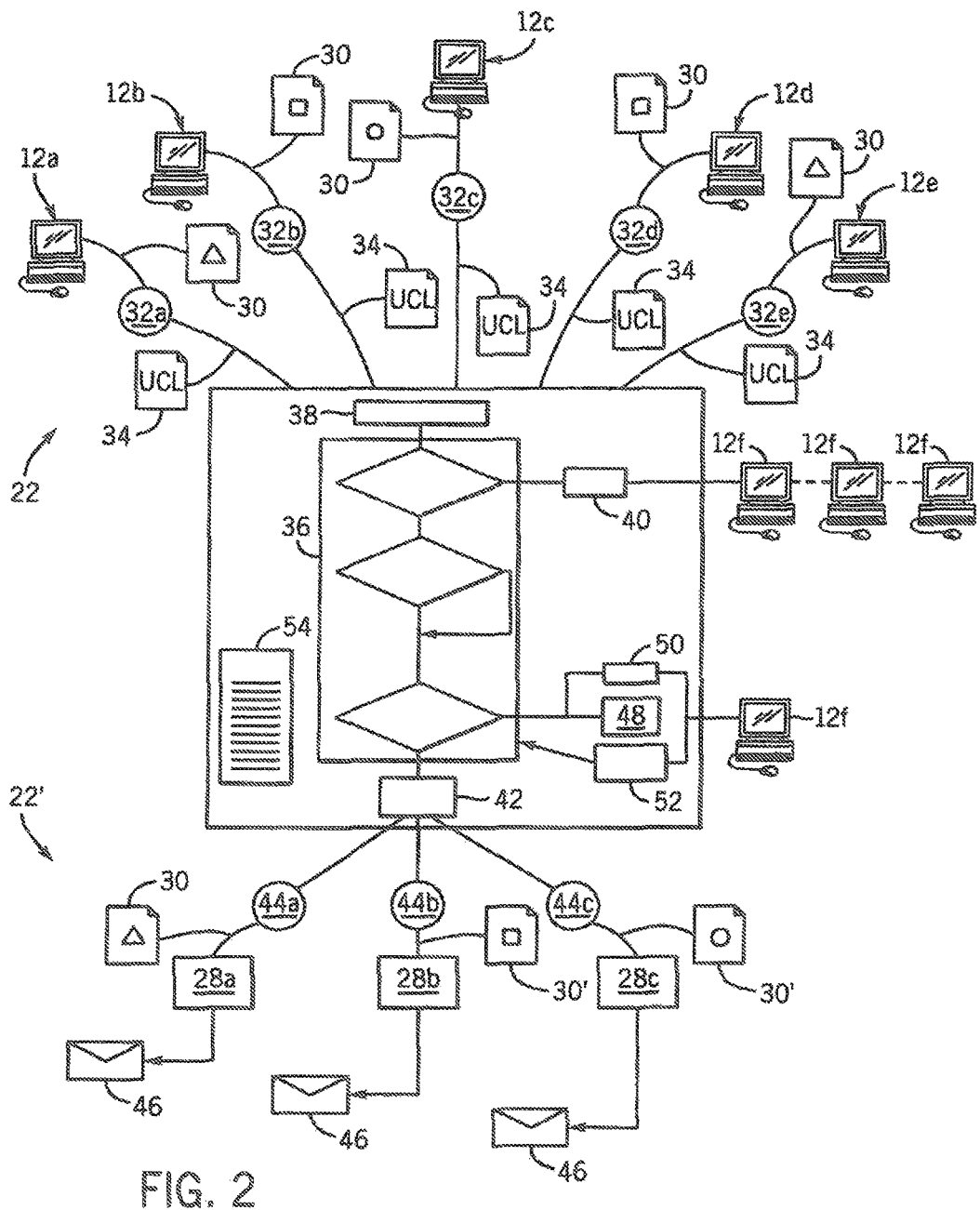
FIG. 2 is a logical block diagram of the billing system of FIG. 1 showing the submitting programs, input translators, rule engines, and output translators that may be used in the present invention.

Referring now to FIG. 2, each of the terminals 12a through 12d may transmit charge data as discrete charges 30 that are formatted for a particular billing program 28 with which the submitting program 14 of the terminal 12 is affiliated. Typically, all charges 30 will include some common charge data, but the order and encoding of the common data will vary among submitting programs 14, and there will be data that is not common among charges 30. The charges 30 may not indicate the particular billing program 28 for which they are intended because in normal operation, a single submitting program 14 will communicate directly with the billing program 28 with which it is associated, and the billing program destination is implicit.

In order to accommodate this variation in the format of charges 30, the present invention provides a series of intake translators 32a through 32e for each format for the charges 30. The intake translators 32a through 32e are programs running in each of the terminals 12a through 12e or within the charge router computer 24 so as to receive all charges 30.

The intake translators 32a through 32e convert each charge 30 to a universal charge line (UCL) 34 having standard data fields, encoding, and formatting and serving as a uniform expression of charge data for all processing by the charge router program 27. The UCLs 34 may have different data (as a function of the data in the associated charge 30), but the data will be organized in the same way so that the charge data may be processed in a uniform manner with the data of different UCLs 34 easily accessed and evaluated. The invention also contemplates that one could create a special submitting program 14 having the ability to directly produce UCLs.

Referring still to FIG. 2 in overview, the charge router program 27 receives each of these UCLs 34 into a staging buffer 38. The staging buffer 38 may, in one embodiment, implement the intake translators 32a through 32e, detecting signatures of charges 30 to identify the necessary translation routine. In alternative embodiment, the submitting programs 14 can be responsible for submitting charges according to a published UCL standard—eliminating the need for separate translation. The staging buffer 38 may, for example, collect and hold charges until a logical billing increment is collected, for example, all charges for a hospital stay. This allows reconciliation of charges and detection of charge errors detectable from the group of charges as described below with respect to the modification rule engine.

From staging buffer 38, the UCLs 34 are passed to a rule engine set 36. A first rule engine of the rule engine set 36 identifies the UCLs 34 that may need review by an operator. These UCLs 34 are forwarded to a work-queue 40 where they are ordered and systematically handled by operators at one or more terminals 12f. A second rule engine of the rule engine set 36 provides automated processing and editing of the UCLs 34 including splitting UCLs 34 that have component charges processed by different billing programs 28. A third rule engine of the rule engine set 36 identifies a destination billing program for the UCLs 34. The UCLs 34 are then forwarded to an output buffer 42 for processing by a series of output translators 44a through 44e. It will be understood from the following description that the present invention is not limited to three rule engines, but that fewer or additional and different rule engines may exist within the framework of the charge router.

The output translators 44a through 44c convert each UCL 34 to charge 30' having a format appropriate to the billing program 28 identified as the destination of the UCL 34. Importantly, the format of the charge 30' may be different from the format of the charge 30 providing the data to the UCL 34 from which the charge 30' is derived. This is because the processing performed by the charge router program 27 may split charges 30 to be sent to different billing programs 28 or redirect charges 30.

The charges 30' are then directed to a particular billing program 28a through 28c per the destinations of the UCLs 34 from which they are derived. The billing programs 28a and 28b then create physical bills 46 to be sent to a patient or an insurance earner.

The charge router program 27 further implements a set of administrative functions including an error pool 48 collecting UCLs 34 which cannot be processed by the rule engine set 36, an administrative data processor 50 for generating reports about the processing of charges 30, and rule builder programs 52 allowing for modification of the rules of the rule engine set 36. A log 54 is also provided logging all or part of each processed UCL 34 for a pre-determined period of time allowing sophisticated tracking and correction of errors. These functions may be accessed by administrative users on terminals 12f and are used by charge correction messages, to be described, that allow changes in charges to be synchronized among the various charge submitters and billing programs or at other places in the charge router.

Figure 4:
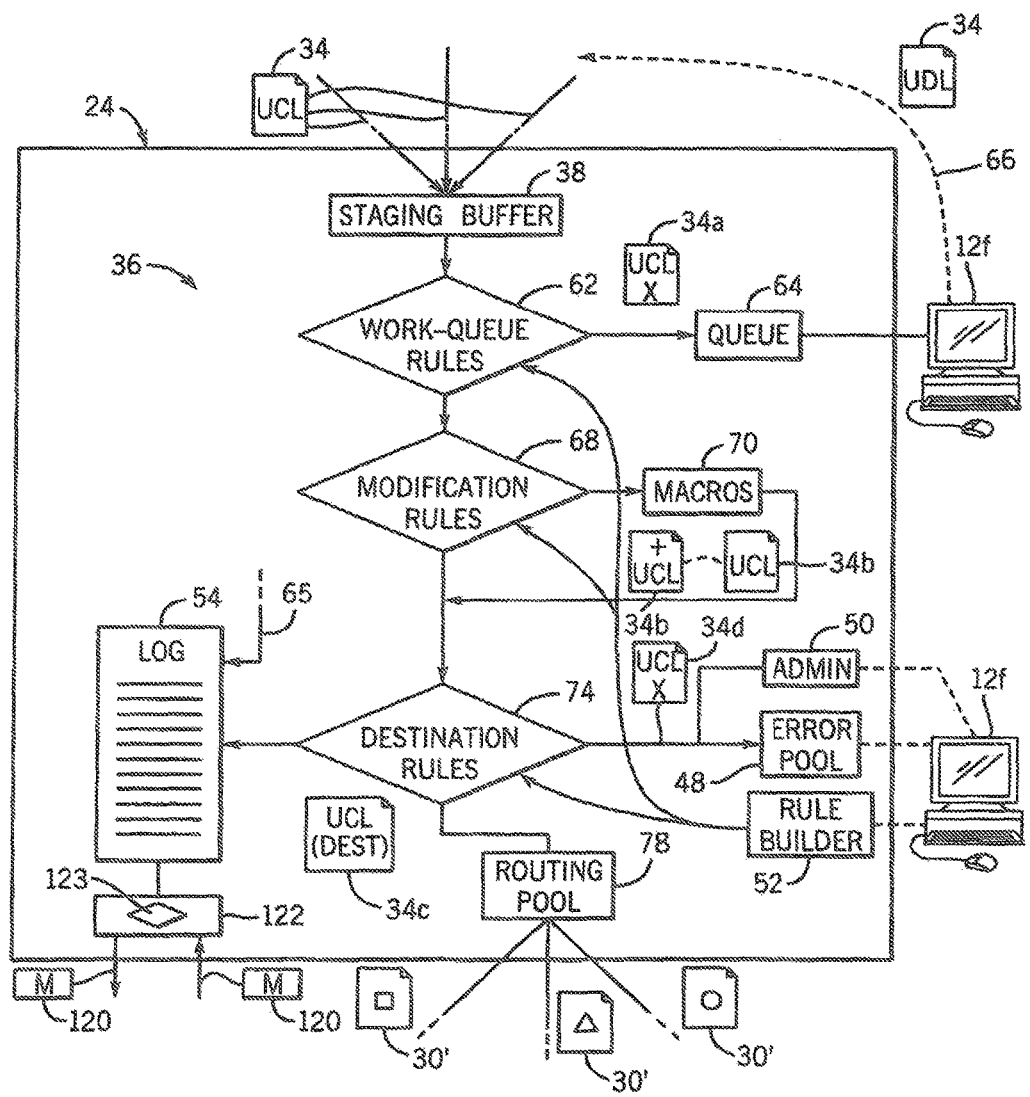
FIG. 4 is a detailed view of the rule engines of FIG. 2 such as process the universal charge record of FIG. 3 also showing other elements of the present invention.

Referring now to FIG. 4, each UCL 34 is first received by a staging buffer 38, which serves to buffer incoming UCLs, place them in order typically by time, but possibly by priority indicated by data in the UCL 34 itself, and to collect UCLs 34 associated with a group. Each such UCL 34 in a group will indicate that it is part of a group (through a data field in the UCL 34), and the final UCL 34 of the group will indicate that it is the final UCL 34 allowing the group to be completed and transmitted downstream.

Figure 3:
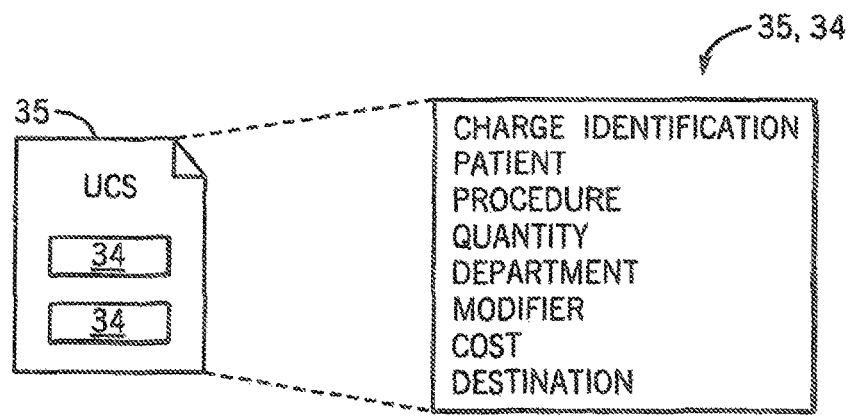
FIG. 3 is a simplified representation of a universal charge record used in the present invention.

As shown in FIG. 3, several UCLs 34 forming part of a group are collected in a universal charge session (UCS) 55 which may hold data shared among the UCLs 34 related to information common about the UCLs 34 and serving to collect the charges in a logical manner. For example, each UCS 55 may include a session identification indicating the group to which the UCLs 34 belong, as well as patient information. Each of the UCLs 34 provide charge specific information such as the particular medical procedure (e.g., ECG, x-ray etc.) by code and description, charge code information, the date and time and place of the procedure, a quantity associated with the procedure (e.g., a number of radiographic films), a department in which the procedure is undertaken, a modifier, for example, those which indicate whether it is a hospital or professionally originated charge, cost information, and a destination information for the UCL 34. Initially, the destination will be blank in most cases and indicates a particular billing program 28a through 28c intended to receive the charge data of the UCL 34.

The fields contained in the UCL 34/UCS 55 are intended to be comprehensive and be a superset of all charge information contained in the charges 30, and may also include other charge information well known to those of ordinary skill in the art such as the billing provider, referral, insurance information, and more. System information may also be included in the UCL 34/UCS 55 such as change status or state, tracking codes, history, and priority. A unique charge identification number may be associated with a particular UCL 34 to facilitate tracking of UCL 34 in the event of a deletion or modification in the future.

Groups collected by the staging buffer 38 and individual UCLs 34 (and/or UCS 55) are then forwarded to the rule engine set 36 and first received by work-queue rule engine 62 which identifies particular UCLs 34 that may require human review. This review is to ensure that the UCLs 34 can be processed by the remaining rule engines of the rule engine set 36 and principally determines whether critical information is missing from the UCL 34. Thus, the work-queue rules written by a user may, in their simplest case, test particular critical fields in the UCL 34 for data and if these fields are empty or null, forward the UCL 34 to a queue 64 for handling by a human operator. The rules thus identify a particular field of the UCL 34, for example, (provider or producer identifier) and if data for that field is missing, forward the UCL 34a to the queue 64. Generating the rules for the work-queue rule engine 62 may be as simple as designating the necessary fields of the UCL 34, and may be done by the user through a rule builder program 52 communicating with an administrative terminal 12f.

The queue 64 includes a charge editor that is handled by one or more human operators on terminals 12f who executes the charge editor program residing on the charge router computer 24 or the terminal 12f′0 to edit the defective UCLs 34a by filling in missing information and resubmit them as indicated by arrow 66 or delete them if necessary. In the preferred embodiment, only a single charge can be edited by a single operator at a time is supported, so that the operator can have complete control over that charge, however, multiple users can access the queue 64 at one time to edit different charges, and in general, multiple users are simultaneously working on the system.

It is anticipated that most UCLs 34 will be complete and will proceed directly to a modification rule engine 68 also providing rules written by the user of the system. Note that the modification rule engine 68 only receives UCLs 34 that are believed to be as complete as possible insofar as the modification rule engine 68 follows the work-queue rule engine 62.

The rules of the modification rule engine 68 fall generally into three different categories: rules that automatically add information to the UCS 34, rules that replace or delete information in the UCL 34, and rules that split the UCL (e.g., create additional UCLs 34). The rules executed by the modification rule engine 68 include two parts. A test section testing for a certain condition based on arguments extracted from the fields of the current UCL 34 or other UCLs and a macro section executing a short script to change the UCL 34 in a pre-determined manner based on the test section and possibly on information in the current UCL 34 and other UCLs 34.

The test section of the rules describes a logical or arithmetic combination of the data of the fields of the UCL 34 using familiar commands such as AND, OR, NOT, =(IS), > (GREATER THAN), and < (LESS THAN). Combinations of logical and arithmetic primitives may also be used as well as more sophisticated operators (such as fuzzy logic operators). The macro section uses macro script instruction such as CLONE, DELETE, SET, FIND, ABORT, APPEND, GET, and FIND OR CREATE, where CLONE creates a new UCL 34 which is an exact copy of the received UCL, 34, DELETE deletes a given UCL 34, SET sets the data in the UCL 34, FIND finds a UCL 34 in the session which matches the given criteria, ABORT ends the macro, APPEND appends given data to a field of the UCL 34, GET returns data value from a field of the UCL 34, and FIND OR CREATE find a procedure with a given procedure code in the session. If none is found, a new UCL 34 is created. Importantly, the macro may look outside the data of the current UCL 34 to other UCLs 34 possibly intended for a different billing program 28. Importantly, the modification rule engine 68 can look at UCLs 34 identified to a single group of charges, a single patient, single provider, or repeated charges. UCLs 34 may be modified by the modification rule engine 68 based on information from another UCL 34. Changes made by the modification rule engine 68 may be communicated to the source of the charges and to the billing programs as desired.

Figure 5:
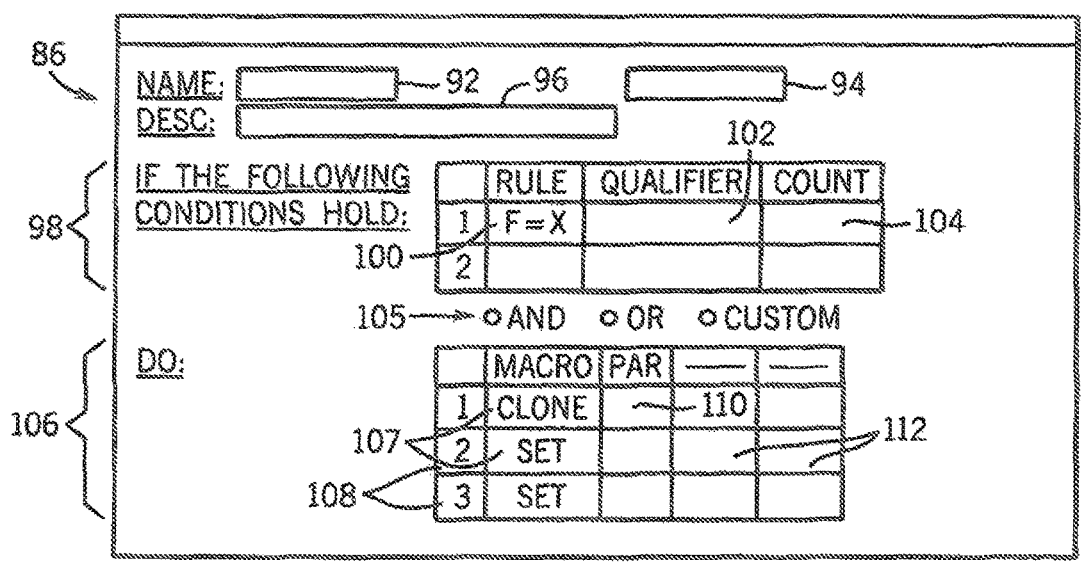
FIG. 5 is an example editor screen used for editing of the rules of the rule engine of FIG. 4 by a user.

As shown in FIG. 5, a given rule for the modification rule engine 68 may be readily generated using the rule builder program 52 which provides a menu screen 80 allowing entry of a rule name at text block 92, which corresponds to underlying data structure for the rule save and used by the charge router program 27. A numeric identifier 94 is automatically developed, typically a sequential number for the rule, for use by the underlying rule builder program 52. A text description of the rule may then be entered by the user to assist others in using and identifying the macro at text entry block 96.

Data for the test section of the rule is then entered in table 98. A comparison portion of the test section may be entered at rule entry block 100. Typically, this comparison portion tests that a field of the UCL 34 has a particular value, the value being either a constant or data based on other fields and/or other UCLs 34. Each comparison portion is associated with state (e.g. true or false) at which the rule is invoked as entered at block 102. Block 104 allows a count of the number of times the rule has been invoked for a particular session to be made into a condition for the rule being invoked this time. That condition (not shown in this example) is entered into block 104.

Multiple comparison portions (defined by the row of blocks 100, 102, and 104) may be combined using the radio buttons 105 invoking logical connectors of AND, OR, and Custom, the latter which provides a more complete set of Boolean primitives to be combined.

If the test section of the rule is satisfied, a macro defined in macro table 106 is invoked involving a set of macro script instructions described above and entered into blocks 107 to be executed according to line numbers 108. Each of the macro instructions of blocks 107 may be associated with one or more parameters entered into parameter blocks 110. Auxiliary fields 112 allow other arguments to be specified.

The modified UCL 34b then proceeds to a destination rule engine 74 which serves to fill in the destination field of FIG. 3 in the UCL 34 as is critical for its forwarding to the necessary billing program 28a or 28b. A typical implementation of a destination rule reviews fields of the UCL 34 to identify the type of procedure and thus the likely billing source. The destination is then imbedded in the UCL 34 to form a comprehensive record of the transaction. The user is provided with complete flexibility to generate rules for the destination rule engine 74 using the rule builder program 52.

An error pool 48 is provided for UCLs 34d where a destination cannot be developed by the destination rule engine 74. Because the destination rules are drafted by individual users at the site, and thus cannot be exhaustively tested by the vendor, an error pool 48 allows treatment of possible rule failure. UCLs 34 in the error pool 48 are reviewed by an administrator and typically will be resolved by correction of the rule and resubmitting of the UCL 34. The error pool 48 is not limited to destination errors, but receives UCLs 34 that cannot be processed for any reason including, but not limited to, formatting errors and missing data. The error pool 48 may separate errors of different types, for example, charges intended for different billing systems either through the use of different error pools or by sorting or filtering techniques. UCLs 34 in the error pool 48 are marked to indicate the source of the error to aid in processing by a human operator. UCLs 34 that have been modified by the charge router program 27, for example, by the modification rule engine 68, are returned to their pre-modification state when they are entered into the error pool 48 to aid in processing by a human operator.

Example I

The East Outpatient Clinic is a hospital-owned ("provider-based") clinic, staffed by non-employed physicians from the Springfield Provider Organization. Medicare charges for visits at the Clinic need to be split into professional fees and facility fees, which are billed by the Springfield Hospital Business Office and the Springfield Provider Organization Business Office, respectively, each having separate billing programs 28. Charges at this clinic are triggered by orders placed by the physicians which generate UCLs 34.

A test section of a rule for Example I implements the following logic:
 IF (Place of Service=East Outpatient Clinic) AND (Payor=Medicare) THEN . . .
where "Place of Service" and "Payor" are predefined fields of the UCL 34.

A macro section for this Example I would be as follow:
 (1) CLONE <UCL>
 (2) SET <result of line 1> modifier="TC". (Add modifier TC to the clone to make it a facility fee.)
 (3) SET <charge> modifier="26". (Add modifier 26 to the original charge to make it the pro fee.)

A destination rule for Example I would be as follows:
 If (Modifier="TC") THEN destination=Resolute Hospital Billing
 IF (Modifier="26") THEN destination=Resolute Professional Billing where "Resolute Hospital Billing" and "Resolute Professional Billing" identify billing programs 28.

Example II

A physician orders an immunization and a UCL 34 is generated. When the nurse administers the immunization, an additional UCL 34 for the administration should be added, however, when there is more than one immunization performed for a given patient on a given date, then the procedure code for the additional administration charges is different from the initial code.

A test section of a rule for Example II implements the following logic:
 IF (Procedure Category=Immunizations) AND (Count of Immunization Charges=1 or >1) THEN . . .
 where count is the accumulated count information described above with respect to block 104 and represents information from multiple UCLs 34.

A macro section for this text section of Example II would be as follows:
 CLONE <charge>
 SET <result of line 1> procedure code="90471". (Change the procedure code of the clone to the admin fee code.)
 SET <result of line 1> procedure description "Admin Immunization".

A second test section of a rule for an Example II implement the following logic:
 IF (Procedure Category=Immunizations) AND (Count of Immunization Charges>1) THEN . . .
 A macro section for this text section of Example II would be as follow: CLONE <charge>
 SET <result of line 1> procedure code="90472". (Change the procedure code of the clone to the additional administrative fee code. In this example, a CPT™ code is used, however, the invention is not limited to such codes.)
 SET <result of line 1> procedure description="Admin Immunization, each additional".
 SET <result of line 1> quantity=(Count of Immunization Charges-1). (Set the quantity to the amount of additional immunizations, minus the initial immunization.)

The UCL 34c with the destination completed is then transmitted to a transmission buffer 78 which provides the output translators 44a through 44c translating the UCL 34c into charges 30' based on the destination information. The charges 30' are then forwarded to the appropriate billing program 28.

The destination rule engine 74 also enrolls the completed UCLs 34c into a log 54 that by recording the completed UCLs 34c provides a history of transactions processed for all of the billing programs 28a through 28c. This data may be held for a pre-determined period of time and then erased. This is only the last step of logging of charge data which also occurs at previous steps of the processing of the UCL 34 as indicated by arrow 65 so as to provide a complete record of that processing.

The centralized processing of charges for multiple billing programs 28 provides for a number of useful administrative functions that may be handled by an operator on terminal 12f. Referring still to FIG. 4, administrative reports may be collected by an administrative data processor 50 providing for an operation summary of the charges processed by the charge router program 27. Typically, this administrative report will indicate UCLs 34 received and UCLs 34 successfully transmitted to ensure that processing is being performed in a prompt manner and may include, for example, the oldest time stamp of a UCL 34 or of the service provided, an indication of the number or percentage of UCLs 34 in the queue 64, total processed UCLs 34, the aging of the UCLs 34 in the queue, the number of UCLs 34 in the error pool. The administrative data processor 50 may also provide the ability to review data in the staging buffer 38, queue 64, error pool 48, and log 54.

Normal report generation features, including limiting reports by dates or by types of UCLs 34 based on the particular information in the UCLs 34, may be obtained as will be understood to those of ordinary skill in the art.

Referring again to FIG. 4, the administrator or other operator or the submitting programs or billing programs may process a charge correction message 120 through the charge router program 27 indicating situations where a UCL 34 previously processed must be deleted or corrected. These charge correction messages 120 need not identify the UCL 34 specifically, but may make use of the charge data associated with the UCL 34, for example, to form a charge 30 or 30'. These messages may be received by a log manager 122 which searches the information of the log 54 to determine the necessary parties where the charge correction message 120 should be routed. For example, a charge correction message 120 from a billing program 28 to delete a charge of a UCL 34 received by the billing program 28 may be received by the log manager 122 which may review the log 54 to match charge information contained in the charge correction message 120 to determine the destinations and/or senders of that UCL 34. This information may be used to route the charge correction message 120 to other processors or senders, particularly to a billing program 28 having received a split UCL 34 based on the instant UCL 34. The log manager 122 may include a set of message rules 123 which automatically modify the charges identified by charge correction messages 120, for example, to effect a change in procedure when a change in charge code is requested. The log manager 122 and log 54 processing charge correction messages 120 thus provide a way to synchronize changes to charges among the various interconnected systems. Generally, the changes requested of a UCL 34 may include deleting the charge, voiding the charge, otherwise changing the charge by marking it "no bill", rejecting the charge or crediting the charge.

The universal overview provided by the charge router program 27 and log 54 may be critical in identifying the necessary message recipients and allows corrections that would normally be difficult to accomplish to be automatically processed.

The features of the charge router described above may be implemented on general purpose computers as programs stored in a memory and operating on data received stored in memory as communicated through standard computer input and output circuits. The actual division of the programs among hardware or functions among programs may be freely varied. It will be understood, however, that some or all of the features of the present invention may also be implemented as dedicated circuitry such as applications specific integrated circuits or as firmware in specialized controllers or the like.

It is specifically intended that the present invention not be limited to the embodiments and illustrations contained herein, but include modified forms of those embodiments including portions of the embodiments and combinations of elements of different embodiments as come within the scope of the following claims.

We claim:

1. A medical billing computer system, comprising:
    a billing computer processor executing instructions stored in a non-transient memory, the instructions including steps for implementing
        a billing input receiving charges including charge data from a billing terminal computer system for at least one of a hospital service area, a medical laboratory, and a professional office of a physician, each charge being an electronic record including a bill for medical services, the bill including an amount to be billed based on a code describing a medical procedure, the bill being formatted by an originating charge source, the bill for medical services including charge data;
        at least one input translator generating one or more universal charges having a common fauna based on the received charge data, the universal charge including the medical procedure code, wherein generating one or more universal charges includes implementing a translation routine for each received charge based on a billing format used by the originating charge source;
        a destination rule engine analyzing the charge data of the universal charges to assign a destination to the universal charges based on the charge data, the destination identifying a billing program; and
        at least one output translator receiving the generated universal charges including assigned destinations from the destination rule engine and converting the universal charges to a billing program format identified in the destination.

2. The medical billing computer system of claim 1 wherein the destination rule engine is configured to determine the destination based on a type of medical service identified in the charge data.

3. The medical billing computer system of claim 1 wherein the charge data is selected from the group consisting of: patient information, procedure information, charge code information, department information, time information, place of service, cost information, and provider information.

4. The medical billing computer system of claim 1 wherein the common format of the universal charges provides a field for information about a destination billing program and wherein the destination vile engine inserts an identified destination into the universal charge from which it is derived.

5. The medical billing computer system of claim 1 wherein the destination rule engine includes a rule editor receiving commands from a user to edit the rules of the rule editor.

6. The medical billing computer system of claim 1 wherein the billing programs require data in different billing program formats.

7. The medical billing computer system of claim 1 wherein the billing programs require data in billing program formats different from the universal charge format.

8. The medical billing computer system of claim 1 wherein the billing computer processor instructions further include steps for implementing a work-queue rule engine analyzing the charge data of the universal charges to detect charges that require human review and enrolling the charge data in a work-queue for review by a human operator before forwarding the charge data to an output translator.

9. The medical billing computer system of claim 8 wherein the work-queue rule engine includes an editor for the work-queue rules.

10. The medical billing computer system of claim 1 wherein the billing computer processor instructions further include steps for implementing an error pool and wherein the destination rule engine further identifies universal charges that cannot be processed by the destination rule engine and enrolls the charge data of any erroneous universal charges in an error pool for editing by a human operator without forwarding the charge data of the erroneous universal charges to an output translator.

11. The medical billing computer system of claim 1 wherein the billing computer processor instructions further include steps for implementing a modification rule engine configured to apply one or more logical rules to the universal charges to modify the charge data of at least one universal charge before forwarding the universal charge to an output translator.

12. The medical billing computer system of claim 11 wherein the billing computer processor instructions further include steps for implementing a log file storing in a searchable database modification made by the modification rule engine to the universal charges.

13. The medical billing computer system of claim 11 wherein the modification rule engine is configured to generate a change correction message based on the modification to the charge data to the charge sources.

14. The medical billing computer system of claim 11 wherein each modification rule includes a test section receiving charge data and testing it for a predetermined test condition and a macro section receiving charge data and modifying it according to a macro script dependant on the test condition, wherein the modification rule engine includes an editor for a user to edit test sections and macro sections.

15. The medical billing computer system of claim 11 wherein the modification is a replacement of a portion of the charge data with different charge data.

16. The medical billing computer system of claim 11 wherein the modification is an addition of charge data.

17. The medical billing computer system of claim 11 wherein the modification is a removal of charge data.

18. The medical billing computer system of claim 11 wherein the modification is an editing of charge data.

19. The medical billing computer system of claim 11 wherein the modification is a creation of a new charge.

20. The medical billing computer system of claim 19 wherein the new charge is intended to be received by a different billing program than the charge from which it was created.

21. The medical billing computer system of claim 11 wherein the modification is based on information from different universal charges.

22. The medical billing computer system of claim 1 wherein the billing computer processor instructions further include steps for implementing an administrative data processor collecting data on a flow of charges through the billing system to create a report providing data fields selected from the group consisting of: charges received, charges successfully transmitted, oldest time stamp of a charge, oldest time stamp of a service provided, an indication of charges in a queue, aging of charges in the queue, and number of charges in an error pool.

23. The medical billing computer system of claim 1 wherein the billing computer processor instructions further include steps for implementing a charge tracking engine configured to determine whether the received charge is associated with at least one additional charge and holding the charge until the at least one additional charge is received.

24. The medical billing computer system of claim 1, wherein the billing computer processor instructions further include steps for propagating changes to charge data by generating a plurality of charge correction messages to be transmitted to the charge source and the identified at least one destination billing program based on the charge tracking data.

25. The medical billing computer system of claim 1, wherein generating one or more universal charges having a common format based on the received charge data, includes generating at least two universal charges for a single received charge splitting the amount of the bill for medical services between two destination billing programs based on the medical procedure code of the received charge.

* * * * *

UNITED STATES PATENT AND TRADEMARK OFFICE
CERTIFICATE OF CORRECTION

PATENT NO. : 10,242,158 B2
APPLICATION NO. : 14/109370
DATED : March 26, 2019
INVENTOR(S) : Mark Robert Lipsky et al.

Page 1 of 1

It is certified that error appears in the above-identified patent and that said Letters Patent is hereby corrected as shown below:

In the Claims

Claim 1, Column 11, Line 61    Delete "fauna" and insert therefor -- format --

Claim 4, Column 12, Line 22    Delete "vile" and insert therefor -- rule --

Signed and Sealed this
Eighteenth Day of June, 2019

Andrei Iancu
*Director of the United States Patent and Trademark Office*